United States Patent
Thyne

(10) Patent No.: US 11,420,214 B2
(45) Date of Patent: Aug. 23, 2022

(54) MODIFIED FLOTATION TEST WITH IN-SITU RESERVOIR CONDITIONS

(71) Applicant: ESAL TECHNOLOGIES, LLC, Laramie, WY (US)

(72) Inventor: Geoffrey Thyne, Laramie, WY (US)

(73) Assignee: ESAL, LLC, Laramie, WY (US)

( * ) Notice: Subject to any disclaimer, the term of this patent is extended or adjusted under 35 U.S.C. 154(b) by 647 days.

(21) Appl. No.: 16/442,253

(22) Filed: Jun. 14, 2019

(65) Prior Publication Data

US 2019/0381517 A1 Dec. 19, 2019

Related U.S. Application Data

(60) Provisional application No. 62/685,648, filed on Jun. 15, 2018.

(51) Int. Cl.
  *B03D 1/00* (2006.01)
  *G01M 13/04* (2019.01)
  *E21B 43/16* (2006.01)

(52) U.S. Cl.
  CPC ............... *B03D 1/00* (2013.01); *E21B 43/16* (2013.01); *G01M 13/04* (2013.01); *B03D 2201/02* (2013.01); *B03D 2203/006* (2013.01)

(58) Field of Classification Search
  CPC ...... G01M 13/04; G01N 13/00; G01N 33/241
  USPC ........................................................ 73/61.51
  See application file for complete search history.

(56) References Cited

U.S. PATENT DOCUMENTS

| 7,255,166 B1 | 8/2007 | Weiss |
| 7,455,109 B2 | 11/2008 | Collins |
| 8,188,012 B2 | 5/2012 | Weerasooriya et al. |
| 8,486,269 B2 | 7/2013 | McGuire |
| 8,812,271 B1 | 8/2014 | Brady et al. |
| 9,518,449 B1 | 12/2016 | Brady et al. |
| 9,727,928 B2 | 8/2017 | Heneman et al. |
| 2010/0096129 A1 | 4/2010 | Hinkel et al. |
| 2011/0256085 A1 | 10/2011 | Talingting Pabalan et al. |
| 2011/0306525 A1 | 12/2011 | Lighthelm |

(Continued)

FOREIGN PATENT DOCUMENTS

| EP | 2179064 | 4/2012 |
| WO | 2010092095 | 8/2010 |

(Continued)

OTHER PUBLICATIONS

Brady et al., "Surface complexation modeling for waterflooding of sandstones," SPE Journal, 2013, vol. 18(2), pp. 214-218, Abstract, 3 pages. 2013.

(Continued)

*Primary Examiner* — Nimeshkumar D Patel
*Assistant Examiner* — Jean F Morello
(74) *Attorney, Agent, or Firm* — Holzer Patel Drennan

(57) ABSTRACT

Measurement of in-situ petroleum reservoir wettability at the current salinity and at different salinities and water compositions. That data may be used to derive the crude oil acid and base equilibrium constants for the oil-surface adhesion reaction that control wettability. These constants may be used in quantitative models of the reservoir wettability. This procedure produces an accurate description of reservoir wettability and identifies the specific water chemistry that will optimize in-situ wettability and, in turn, oil production.

20 Claims, 10 Drawing Sheets

(56) References Cited

U.S. PATENT DOCUMENTS

| | | | |
|---|---|---|---|
| 2012/0067579 A1 | 3/2012 | Pich et al. | |
| 2012/0125603 A1 | 5/2012 | Willingham et al. | |
| 2012/0125605 A1 | 5/2012 | Willingham et al. | |
| 2014/0262275 A1 | 9/2014 | Dean et al. | |
| 2015/0096757 A1* | 4/2015 | Thyne ................ | G01N 33/1846 166/307 |
| 2017/0356281 A1 | 12/2017 | Brady et al. | |

FOREIGN PATENT DOCUMENTS

| | | |
|---|---|---|
| WO | 2014158906 | 10/2014 |
| WO | 2016105395 | 6/2016 |

OTHER PUBLICATIONS

Dubey et al., "Base No. and Wetting Properties of Crude Oil," SPE Reservoir Engineering,1993, vol. 8(3), pp. 195-200, Abstract, 3 pages. 1993.

Chemical Verification of the EOR Mechanism by Using Low Saline/Smart Water in Sandstone Alireza RezaeiDoust, Tina Puntervold, and Tor Austad Energy & Fuels 2011 25 (5), 2151-2162, Mar. 31, 2011. 2011.

Anderson, William G. "Wettability Literature Survey Part 2: Wettability Measurement." Conoco, Inc. 1986. Journal of Petrolum Technology. 1986.

Abdallah, Wael et al. "Fundamentals of Wettability." Oilfield Review. 2007. 2007.

Anderson, William G. "Wettability Literature Survey Part 1: Rock/Oil/Brine Interactionas and the Effects of Core Handing on Wettability." Conoco, Inc. 1986. Journal of Petrolum Technology. 1986.

Brady, Patrick V. and Thyne, Geoffrey. "Functional Wettability in Carbonate Reservoirs" Energy & Fuels. ACS Publications. Oct. 11, 2016.

Brady, Patrick V. et al. "Altering wettability to recover more oil from tight formations." Journal of Unconventional Oil and Gas Resources 15. 79-83. 2016. Elsevier Ltd. 2016.

Brady, Patrick V. et al. "Surface Complexation Modeling for Improved Oil Recovery." SPE International. 14-18. Oil Recovery Symposium. Apr. 2012. Apr. 2012.

Buckley, J.S. and Liu, L. "Some mechanisms of crude oil/brine/solid interactions." Petroleum Recolery Research Center, NM Institute of Mining and Technology. Jan. 21, 1998.

Buckley, Jill S. "Effective wettability of minerals exposed to crude oil." Current Opinion in Colloid & Interface Science 6. 2001. 191-196. Elsevier. 2001.

Celik, M.S. and Somasundaran, P. "Effect of Pretreatments on Flotation and Electrokinetic Properties of Coal." Elsevier Scientific Publising Company. Colloids and Surfaces, 1 (1980) 121-124. 1980.

Drummond, Carlos and Israelachvili, Jacob. "Fundamental studies of crude oil-surface water interactions and its relationship to reservoir wettability." Journal of Petroleum Science and Engineering 45 (2004) 61-81. Elsevier. 2004.

Dubey, S.T. and Doe, P.H. "Base Number and Wetting Properties of Crude Oils." SPE Reservoir Engineering. Aug. 1993.

Erzuah, S. et al. "Wettability Characterization Using the Flotation Technique Coupled with Geochemical Simulation." The National IOR Centre of Norway. 19th European Symposium on Improved Oil Recovery. 24-27. EAGE. Apr. 2017.

Hirasaki, G.J. "Wettability: Fundamentals and Surface Forces." SPE Formulation Evaluation. Jun. 1991.

Kaszuba, John P. et al. "Supercritical carbon dioxide and sulfur in the Madison Limestone: A natural analog in southwest Wyoming for geologic carbon-sulfur co-sequestration." Earth and Planetary Science Letters 309 (2011) 131-140. Elsevier. 2011.

Mwangi, Paulina et al. "The effect of organic acids on wettability of sandstone and carbonate rocks." Journal of Petroleum Science and Engineering 165 (2018) 428-435. Elsevier. 2018.

Qiao, Chenghe. "Understanding the Chemical Mechanisms for Low Salinity Waterflooding." SPE Europec featured at 78th EAGE Conference and Exhibition. Jun. 22, 2016.

Mwangi, Paulina et al. "Extensive Experimental Wettability Study in Sandstone and Carbonate-Oil-Brine Systems: Part 1—Screening Tool Development." International Symposium of the Society of Core Analysts. Sep. 2013.

Skold, Mangus. "Using UCODE_2005 and PHREEQC to Determine Thermodynamic Constants from Experimental Data." Ground Water. vol. 45, No. 3. Jun. 2007.

Smith, J.T. and Ehrenberg, S.N. "Correlation of carbon dioxide abundance with temperature in clastic hydrocarbon reservoirs: relationship to inorganic chemical equilibrium." Marine and Petroleum Geology, 1989, vol. 6. May 1989.

Thyne, Geoffrey. "Wettability Alteration in Reservoirs: How it Applies to Alaskan Oil Production." Society of Petroleum Engineers. 2016.

Sohal, M. Adeel, et al. "Novel Application of the Flotation Technique to Measure the Wettability Changes by Ionically Modified Water for Improved Oil Recovery in Carbonates." ACS Publications. Energy & Fuels. 2016.

Fjelde, Ingebret et al. "Screeing of the Potential for Different Injection Water Compositions to Alter Wettability to More Water-Wet." Society of Petroleum Engineers. 2017.

Erzuah, Samuel et al. "Wettability Estimation by Surface Complexation Simulations." SPE Europec. EAGE Conference and Exhibition. Jun. 2017.

Thyne, Geoffrey. "A Review of the Measurement of Wettability." Science Based Solutions LLC. 2016.

Thyne, Geoffrey and Brady, Patrick. "Evaluation of formation water chemistry and scale prediction: Bakken Shale." Applied Geochemistry 75 (2016) 107-113. Elsevier. 2016.

Wu, Yongfu et al. "An Experimental Study of Wetting Behavior and Surfactant EOR in Carbonates With Model Compounds." SPE Journal. Mar. 2008.

Gamage et al., "Comparison of Oil Recovery by Low Salinity Waterflooding in Secondary and Tertiary Recovery Modes" SPE International. 2011.

Salathiel et al., "Oil Recovery by Surface Film Drainage in Mixed-Wettability Rocks," Journal of Petroleumm Technology. 1216-1224. Oct. 1973.

Thyne et al. "Evaluation of the Effect of Low Salinity Waterflooding for 26 Fields in Wyoming." SPE International. 2011.

* cited by examiner

MODIFIED FLOTATION TEST WITH IN-SITU RESERVOIR CONDITIONS

RELATED APPLICATIONS

This application claims priority under 35 U.S.C. § 119(e) to U.S. Provisional Application Ser. No. 62/685,648, filed on Jun. 15, 2018, which is incorporated in its entirety herein by reference.

FIELD

The present disclosure generally relates to testing approaches that may be used in relation to oil reservoirs, and in particular to wettability testing of an oil reservoir.

BACKGROUND

On average, conventional oil production methods will only produce about 30% of the initial oil in place from a petroleum reservoir. The remaining oil (e.g., liquid hydrocarbons), nearly 70% of the initial petroleum resource, is a large and attractive target for oil recovery methods. Initial production (primary) refers to the spontaneous production that utilize natural reservoir energy. Secondary oil recovery refers to oil production from injection of water (waterflooding) which utilize reservoir repressurizing schemes with injected water to increase reservoir pressure and displace more oil. Tertiary oil recovery, or other enhanced oil recovery refers to the process of producing liquid hydrocarbons by methods other than the conventional use of reservoir energy or water floods.

In the field of oil recovery there remains a significant need for producing efficient and cost-effective methods to change wettability to increase recovery, and methods for applying said compositions to subterranean rock formations, wherein the composition is specifically designed for to alter the wettability of the reservoir for the purpose of maximizing recovery.

SUMMARY

One factor related to the ability to recover more oil from an oil reservoir is the wettability of the reservoir. Wettability can impact recovery at any stage of production. Wettability describes the preference of a solid surface to be in contact with one fluid rather than another fluid. This preference is based on atomic-scale surface and interfacial forces (e.g., van der Waals, electrostatic, and steric forces). Since it is not possible to independently measure these three forces, wettability is usually measured by the macroscopic scale expression of the forces. An example would be how high the liquid in a glass tube is drawn above the liquid in the glass. This macroscale observation is the wetting of the glass tube by water as the water displaces air.

Wettability in the context of an oil reservoir refers to the adhesion of crude oil to the rock surfaces. The wettability of the oil reservoir of interest can affect the efficiency of waterflooding operations. The surfaces in the petroleum reservoir are dominantly mineral grains with some associated organic matter. The fluids are water, which is usually saline brine, and crude oil (a mixture of numerous non-aqueous liquid and gaseous hydrocarbons). If oil adheres to the mineral surfaces, we identify the system as oil-wet. In contrast, if the oil does not adhere to the mineral surfaces, the system is considered water-wet. Most petroleum reservoirs have a combination of oil-wet and water-wet surfaces based on localized reservoir conditions. In turn, while the wettability of a system may affect oil recovery methods, it may be difficult to accurately measure or predict the in-situ wettability of the system.

It is presently recognized that the physical characteristics and oil and water chemistry of an oil reservoir of interest play an important role in the wettability of the oil reservoir. Understanding these characteristics and chemistry may allow for more accurate measurement of the reservoir wettability. Additionally, with the ability to accurately measure the reservoir wettability, it may be easier to evaluate modifications to the wettability in such systems. Specifically, oil production may be enhanced by modifying the wettability of an injected water for use in oil recovery. It is presently recognized that replication of in-situ reservoir conditions (e.g., including pH) may allow for more accurate measurement of wettability in a system designed to model oil reservoir behavior (e.g., for evaluation of an oil reservoir's potential for oil recovery and/or for design of improved oil recovery operations). Specifically, the present disclosure recognizes the effect of pH on the wettability of an oil reservoir. Accordingly, wettability testing is described herein that may accurately reflect pH conditions of an oil reservoir of interest. In turn, more accurate wettability measurements maybe provided, which may assist in evaluating techniques designed to modify the wettability for oil recovery from the reservoir. The term "oil" is used throughout this disclosure. It should be understood that "oil" may encompass any non-aqueous phase liquid (NAPL). As such, where the term oil may be interchanged with NAPL throughout this disclosure. Furthermore, it should be appreciated that in some contexts "oil" may include liquid and/or gas components. In other contexts, "oil" may refer to a degassed oil. The "oil" may comprise crude oil. "Oil" may also refer to an extract or component of crude oil including, for example, a liquid extract of crude oil. The "oil" may contain hydrocarbon and non-hydrocarbon components.

Accordingly, the following description includes an explanation of the importance of controlling certain variables in a wettability test and presents an improved testing procedure. In addition, as the conditions corresponding to the oil reservoir may be controlled, the response to various changes (e.g., to the aqueous phase or brine of the reservoir) may be more accurately predicted. This may assist in designing injected water to favorably modify the wettability of the oil reservoir for oil production. The modified injected water used in oil recovery may be used in primary recovery, secondary recovery, tertiary recovery, or any other oil production phase or process including any enhanced oil recovery techniques. Furthermore, the improved testing procedure may be extended to assist in development of equilibrium constants that may be used in relation to geochemical models of reservoir wettability.

In relation to wettability of an oil reservoir of interest, a number of important factors relate to the effectiveness of oil recovery from a reservoir. The macroscopic effect is that some of the crude oil or non-aqueous phase liquid (NAPL) "wets" the rock and does not move during normal production practices. This adhesion of oil to rock helps limit recovery in most reservoirs to an average of 30-35% of the initial oil-in-place. In the oil reservoir, some of the oil will directly contact the mineral surfaces and adhere, creating hydrophobic zones where oil can adhere, thus impeding oil recovery in the reservoir.

But much of the oil wetting takes place between oil and mineral surfaces separated by a water film. The mineral surfaces have an electrostatic charge, as do the polar portions of crude oil (the organic acids and bases in the oil). These electrostatic forces may be attractive or repulsive, thus promoting or discouraging oil adhering to the rock.

The organic acids and bases in crude oil are organic frameworks (carbon and hydrogen) with polar groups containing oxygen, nitrogen and sulfur. The carbon and hydrogen portions of the molecule will remain in the bulk oil phase while the polar portions will tend to migrate to the oil-water interface. The polar portions of oil are only a few percent of the total oil, but the polar portions serve as anchors to the mineral surface sites allowing the non-polar portions of the oil to wet (e.g., adhere to) the rock due to the attractive forces acting between the mineral surface and the polar portions of the oil acting through the water film. It has been found that this type of wetting is reversible or transient depending on the electrostatic forces. Specifically, if the surface charges on oil and/or mineral surfaces are altered, the wettability of the system may be changed such that the oil that adheres to the mineral surface may be released allowing for recovery of additional oil from the reservoir.

However, it is also recognized herein that the in-situ reservoir pH may affect the wettability in view of the foregoing understanding regarding the interaction between the polar portion of the oil and the charged mineral surfaces in the reservoir. The term reservoir pH may refer to the in-situ pH of the reservoir brine or the pH of the reservoir generally including all phases present therein. As such, the term in-situ reservoir pH and reservoir pH may be used interchangeable throughout this disclosure to refer to the pH of the oil reservoir of interest.

In view of the foregoing, it is presently recognized that the wettability of oil reservoirs is dependent, at least in part, on the polarity of mineral and oil surface charges, which are in turn dependent on reservoir pH. This means the wettability of oil in petroleum reservoirs can be directly related to reservoir pH through a set of chemical reactions between reservoir surfaces and the polar portions of the oil. In turn, it is recognized that it is advantageous to control a wettability test to reflect reservoir pH to achieve more accurate results. Accordingly, the following disclosure presents wettability testing procedures in which the experimental pH of the test vessel is controlled to replicate reservoir pH to provide more accurate wettability results for characterization of the oil reservoir and evaluation of techniques designed to modify the wettability of the oil reservoir. While the present disclosure primarily discusses a modified flotation test, it may be appreciated that the influence of pH on the wettability test may be generally extrapolated to any test designed to determine the wettability of an oil reservoir. A first aspect of the disclosure includes a method for performing a modified flotation test of a system corresponding to an oil reservoir of interest. The method includes adding a number of samples to a test vessel. The samples include a solid phase sample, an aqueous phase sample, a gas phase sample, and an oil sample. The solid phase sample includes reservoir rock or geologically analogous rock corresponding to the oil reservoir of interest. The aqueous phase sample corresponds to reservoir formation water found in the oil reservoir of interest. The gas phase sample corresponds to a gas phase of the oil reservoir of interest. The oil sample may include a crude oil sample or degassed crude oil sample. In any regard, the oil sample corresponds to an oil of the oil reservoir of interest. In turn, the method also includes controlling a chemistry of the gas/liquid phase sample to achieve an experimental pH value in the test vessel corresponding to conditions of the oil reservoir of interest and allowing contents of the test vessel, after the adding step, to reside for at least a first residence time period while maintaining the experimental pH value in the test vessel corresponding to the oil reservoir of interest based on control of the chemistry of the gas/liquid phase in the test vessel. Thereafter, the method includes separating a first subset of solid phase sample particles in the aqueous phase sample from a second subset of solid phase sample particles in the oil sample from the test vessel after the first residence time period and measuring the relative amounts of the first subset of solid phase sample particles relative to the second subset of solid phase sample particles to determine a measure of the wettability of the system.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For instance, the solid phase sample, the aqueous phase sample, the oil sample, and the gas phase sample may be provided in the test vessel at a volumetric ratio approximating a relative ratio of the reservoir rock, reservoir formation water, the gas phase, and the oil in the reservoir of interest. In an example, the solid phase sample, the aqueous phase sample, the oil sample, and the gas phase sample may be provided in the test vessel at a volumetric ratio of about 1:10:3:20.

In relation to the solid phase sample, the method may also include sizing the reservoir rock particles corresponding to the oil reservoir of interest to allow surface forces to dominate the wettability of the system. For instance, the method may include grinding the reservoir rock corresponding to the oil reservoir of interest into a fine powder. In an example, the reservoir rock corresponding to the oil reservoir of interest may be a sample obtained directly from the oil reservoir of interest. The reservoir rock corresponding to the oil reservoir of interest may include at least one of a sandstone, limestone, dolomite, chalk, chert, carbonate, another oil bearing geological media, or a combination thereof. In one specific context, the reservoir rock corresponding to the oil reservoir of interest may be a shale containing oil.

In an example, the aqueous phase sample may be a produced water obtained directly from the oil reservoir of interest. Alternatively, the aqueous phase sample may include a synthesized water (e.g., a synthetic water with the same or similar water chemistry as the produced water). The synthesized water may comprise a first water (e.g., produced water obtained directly from the reservoir of interest or a synthetic water with the same or similar water chemistry) mixed with a second water. The synthesized water may differ with respect to the produced water in at least one chemical characteristic. For example, the synthesized water may differ with respect to the produced water at least with respect to an amount of total dissolved solids (TDS). In various examples, the amount of TDS of the synthesized water may be greater than or less than the amount of TDS in the produced water. As will be described in greater detail below, this may assist in the evaluation of synthesized water that may be injected into the oil reservoir to modify the wettability for improvement to an oil recovery operation.

In an example, the oil sample may be the oil obtained directly from the oil reservoir of interest. In this regard, the oil sample may comprise crude oil. In one context, the oil sample may be an extract of crude oil. In an example, the extract of crude oil may be a liquid extract of crude oil.

Alternatively, the oil sample may be a synthesized oil sample having at least one property in common with the oil of the oil reservoir of interest.

In an example, the gas phase may be atmospheric gas comprising nitrogen, oxygen, argon, and carbon dioxide. Furthermore, controlling the chemistry of the gas phase may include control of at least one of a composition, a temperature, or a pressure of the gas phase. For instance, controlling the chemistry of the gas phase may include maintaining a vessel partial pressure of carbon dioxide in the test vessel at a level corresponding to a reservoir partial pressure of carbon dioxide in the reservoir of interest. As is described in greater detail below, this partial pressure of carbon dioxide may influence the resulting experimental pH in the test vessel, thus allowing the experimental pH to be maintained at or near in-situ reservoir pH. The gas phase may be maintained at a pressure of not less than about 10 psi and not greater than a maximum pressure in the reservoir of interest. In one particular context, the gas phase may be maintained at a pressure of not less than about 10 psi and not greater than a maximum hydrostatic pressure gradient of the system. In either of the foregoing instances, the lower bound of the range may alternatively comprise atmospheric pressure.

In an example, the method may include performing a series of tests on a plurality of test vessels to determine a manner in which the wettability of the oil reservoir of interest changes with a changed parameter. This may include determining an equilibrium constant that describes one or more reactions of the oil reservoir as described by a geochemical model. Accordingly, the method may include preparing a plurality of test vessels, where each of the plurality of test vessels may include a unique respective aqueous phase sample (e.g., a chemically unique sample). For instance, the unique respective aqueous phase samples may each be chemically unique such that at least one chemical property differs for different ones of the respective aqueous phase samples. Each corresponding one of the unique respective aqueous phase samples may, for example, differ with respect to at least one of an amount of total dissolved solids (TDS). In turn, the method may include measuring the relative amounts of the first subset of solid phase sample particles relative to the second subset of solid phase sample particles for each of the plurality of test vessels. Based on the results of the measuring, the method may also include determining an equilibrium constant regarding the wettability of a system comprising the reservoir rock, the reservoir formation water, and the oil of the reservoir of interest based on the relative amounts of the first subset of solid phase sample particles relative to the second subset of solid phase sample particles for each of the plurality of test vessels. For instance, the results of the measuring may be used to fit a curve to the data to determine the equilibrium constant. The equilibrium constant may relate to a computational model regarding the reservoir of interest, and the method may also include using the equilibrium constant in the computational model for determining at least one property of an injected water for injection into the reservoir of interest to interact with a subterranean hydrocarbon reservoir of the reservoir of interest in a primary recovery operation, secondary recovery operation, tertiary recovery operation, or any other enhanced production operation. For instance, it is recognized that a balanced oil-wet/water-wet system (e.g., where the oil reservoir is as equally oil-wet as it is water-wet) may optimize oil recovery. As such, the injected water may achieve a balanced oil-wet/water-wet oil reservoir as a result of the injection of the injected water (e.g., according to a designed water chemistry as described herein) injected into the oil reservoir. The at least one property may include an amount of total dissolved solids (TDS). The determining the at least one property of the injected water may include determining an alteration to a produced water of the reservoir of interest to obtain the injected water. This alteration may include mixing the produced water with a second water.

Moreover, the various test vessels prepared to generate the equilibrium constant may be specifically designed to be acidic or basic in nature. In this regard, reactions in the test vessel due to reactions involving acids or reactions involving bases may be isolated in respective ones of the plurality of test vessels by controlling the pH of the test vessels. Accordingly, an acid equilibrium constant and a base equilibrium constant may be determined based on respective ones of the basic test vessels and the acidic test vessels (e.g., from data collected in relation to a wettability test of the respective ones of the basic test vessels and/or the acidic test vessels). As such, in one particular context, the equilibrium constant may be an acid equilibrium constant derived by a plurality of basic test vessels having a pH greater than 7, greater than 8, or even greater than 9. Alternatively, the equilibrium constant may be a base equilibrium constant derived by a plurality of acidic test vessels having a pH less than 5, less than 4, or even less than 3. Moreover, the equilibrium constant may be an acid equilibrium constant derived by a plurality of basic test vessels having a pH greater than 7, greater than 8, or 9 or greater and a base equilibrium constant derived by a plurality of acidic test vessels having a pH less than 5, less than 4, or 3 or less. Additionally or alternatively, the method may include preparing and measuring a plurality of test vessels as described above and determining, based on the relative amounts of the first subset of solid phase sample particles relative to the second subset of solid phase sample particles for each of the plurality of test vessels, a given one of the unique respective aqueous phase samples that provides a nearest approximation of the first subset of solid phase sample particles and the second subset of solid phase sample particles being equal in relative amounts. This may include determining at least one property of an injected water for injection into the reservoir of interest to interact with a subterranean hydrocarbon reservoir of the reservoir of interest in a production operation (e.g., during primary, secondary, and/or tertiary recovery) based on the given one of the unique respective aqueous phase samples (e.g., to achieve a balanced oil-wet/water-wet system). In an example, the contents of the test vessel may come to an equilibrium during the first residence time period. Additionally, the method may further include expressing the wettability of the system as determined in the measuring step as a wettability value in relation to a wettability index, such as, for example, an Amott index with values that range from −1 to +1.

A second aspect of the present disclosure includes a method for performing a modified flotation test for an oil reservoir of interest. The method includes preparing a plurality of test vessels by adding to each of the plurality of test vessels a solid phase sample comprising reservoir rock corresponding to the oil reservoir of interest, a gas phase sample that corresponds to a gas phase of the oil reservoir of interest, and an oil sample. In turn, the method includes adding to each one of the plurality of test vessels a corresponding aqueous phase sample. Each corresponding aqueous phase samples differs with respect to a value for total dissolved solids (TDS). The method further includes maintaining each of the plurality of test vessels at a condition to produce within each test vessel an experimental pH value corresponding to the pH of the oil reservoir of interest and allowing each of the plurality of test vessels to reside for a residence time period within the test vessel while maintaining the experimental pH value of the oil reservoir of interest based on control of a chemistry of the gas phase sample. In turn, the method includes separating from each of the plurality of test vessels after the residence time period a first subset of solid phase sample particles in the aqueous phase sample from a second subset of solid phase sample particles in the oil sample and measuring the relative amounts of the first subset of solid phase sample particles relative to the second subset of solid phase sample particles for each of the plurality of test vessels. Thereafter, the method includes calculating at least one equilibrium constant regarding the wettability of a system comprising the reservoir rock, the reservoir formation water, and the oil of the reservoir of interest based on the relative amounts of the first subset of solid phase sample particles relative to the second subset of solid phase sample particles for each of the plurality of test vessels.

A number of feature refinements and additional features are applicable to the second aspect. These feature refinements and additional features may be used individually or in any combination. As such, each of the foregoing features that were discussed in relation to the first aspect may be, but are not required to be, used with any other feature or combination of features of the second aspect.

A third aspect of the present disclosure includes a method for increasing oil recovery from a subterranean hydrocarbon reservoir formation. The method includes injecting an injection water into the subterranean hydrocarbon reservoir formation at an injection well, where the injection water interacts with the subterranean hydrocarbon reservoir formation, and where the injection water comprises a recovery index value. The recovery index value corresponds to a wettability of the hydrocarbon reservoir formation in the presence of the injection water as determined by a modified flotation test according to any of the foregoing first or second aspects.

A number of feature refinements and additional features are applicable to the third aspect. These feature refinements and additional features may be used individually or in any combination. As such, each of the following features that will be discussed may be, but are not required to be, used with any other feature or combination of features of the third aspect. For instance, any of the feature refinements or additional features described above in relation to the first aspect may be used in any combination with respect to the third aspect.

Additionally, in an example the method may also include recovering the injection water and a hydrocarbon from the subterranean hydrocarbon reservoir at a production well. The method may also include mixing produced water with a second water to generate the injection water. The recovery index value may be an indication that the injected water interacts with the subterranean hydrocarbon reservoir formation to result in the subterranean hydrocarbon reservoir formation being equally water wet and oil wet.

DETAILED DESCRIPTION

Figure 1:
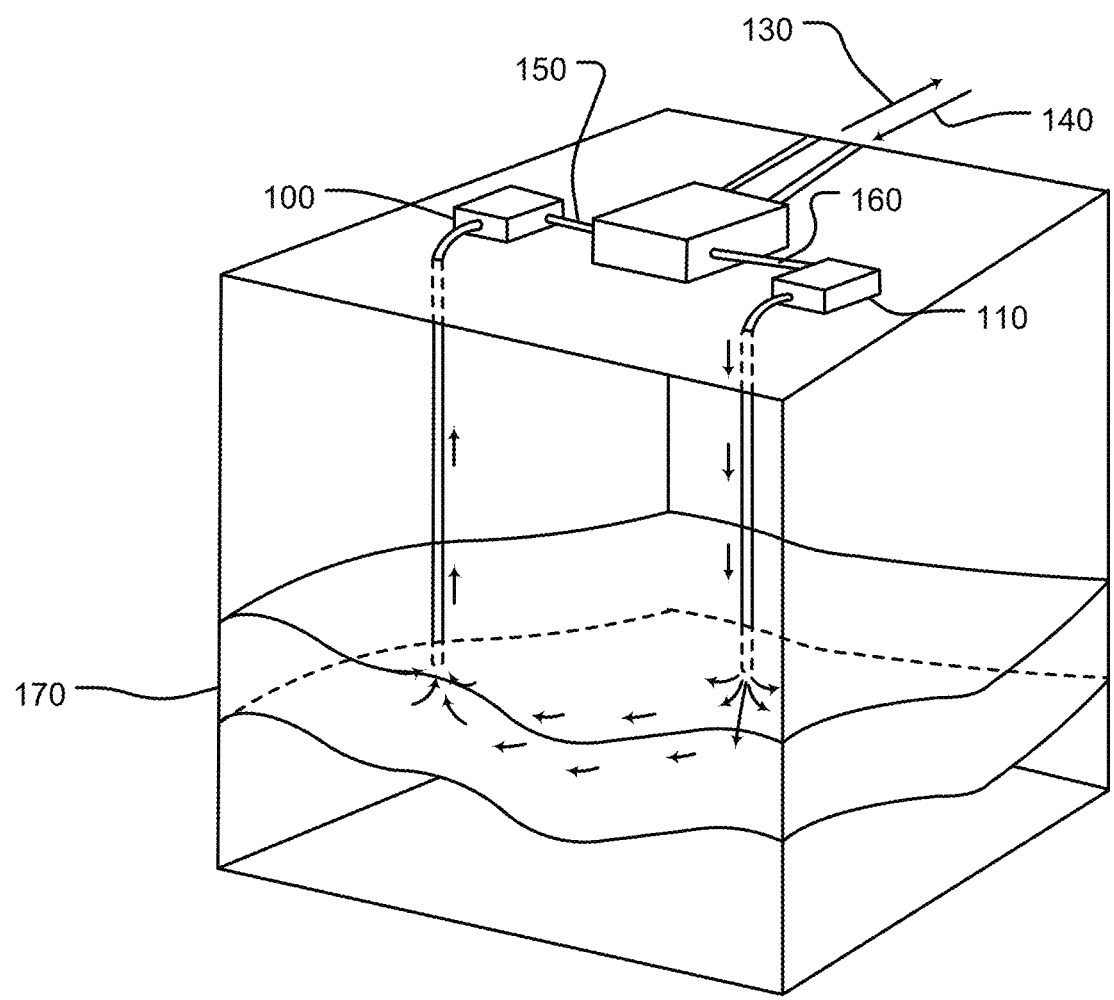
FIG. 1 shows one example of an oil recovery system comprising a producing well and an injection well and a dilution stream for enhancing oil recovery.

While the disclosure is susceptible to various modifications and alternative forms, specific examples thereof have been shown by way of example in the drawings and are herein described in detail. It should be understood, however, that it is not intended to limit the disclosure to the particular form disclosed, but rather, the disclosure is to cover all modifications, equivalents, and alternatives falling within the scope of the disclosure as defined by the claims.

With reference to FIG. 1, one example of an oil recovery method is shown. An oil reservoir 175 in a rock formation 170 may be perfused with an injected water 160, whereby the injected water is supplied to the reservoir by an injection well 110. The injected water 160 flows through the oil reservoir 175 and intermingles with formation water and extracts oil from the formation to create a produced water containing oil 150. This oil/water mixture comprising the produced water containing oil 150 flows out of the rock formation and back to the surface by a producing well 100. Alternatively, single well operation may be used in which injected water 160 is introduced and removed through a common well (e.g., injection well 110). In any regard, the produced water containing oil 150, is then transported to a processing station 120 where the oil is separated from the water. This separation step results in an oil product stream 130. The separation step also results in a produced water stream (not shown) that, in at least some examples, may be altered with another water 140, which results in the injected water 160, which is now modified to optimize oil recovery from the rock formation. This may assist in efficiency of operations by utilizing recovered produced water to produce the injected water 160.

Figure 2:
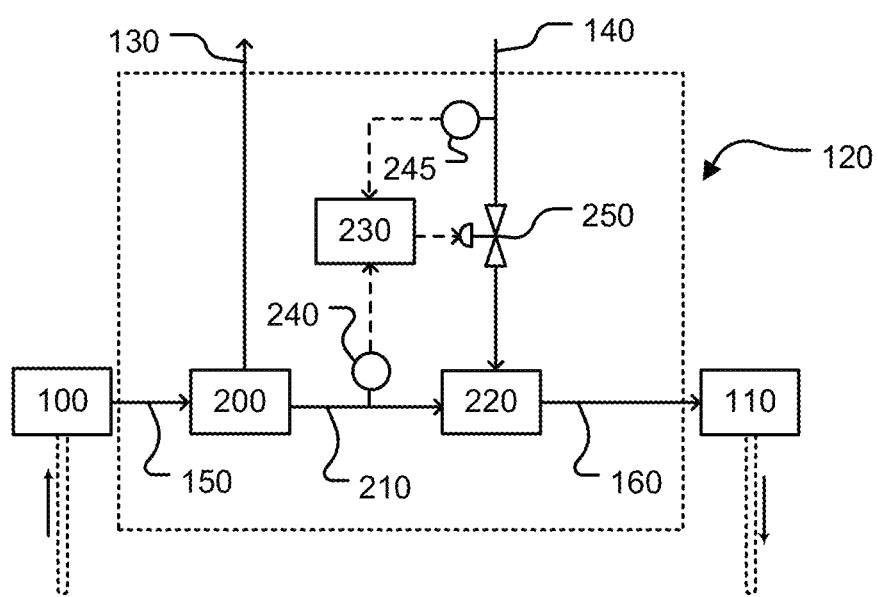
FIG. 2 illustrates one example of a block diagram of a processing station for adding a dilution water to a produced water to facilitate oil recovery.

With further reference to FIG. 2, one example of a processing station 120 for producing an injected water 160 is shown. The produced water containing oil 150 may be transported to the surface of the producing well 100, where it is fed to an oil/water separator 200. This may be a gravimetric separator. The oil/water separator may produce an oil product stream 130 and a produced water stream 210. At least one measurement device 240 may analyze the produced water stream. Metrics analyzed by the at least one measurement device may include, but are not limited to, pH, salinity, total dissolved solids (TDS), ion concentration, osmotic strength, flow rate, and temperature. These metrics may then be communicated to a control center 230.

The control center 230 may comprise a computer system on which may be located at least one equilibrium model or algorithm. An alteration water stream 140 may also enter the processing station 120. This alteration water stream 140 may also be analyzed by at least one measurement device 245. Like the at least one measurement device 240 for the produced water stream 210, the at least one measurement device 245 for the alteration water stream 140 may measure metrics such as pH, salinity, TDS, ion concentration, osmotic strength, flow rate, and temperature. These alteration water metrics may also be communicated to the control center 230. With both the produced water metrics and the alteration water metrics defined, the at least one equilibrium model or algorithm may then calculate at least one optimum target injected water 160 metric for optimizing oil recovery from the well. As will be described in greater detail below, the optimum target injected water 160 (e.g., a property thereof such as TDS) may be determined in relation to the performance of a wettability test, such as a modified flotation test, in which the experimental pH maintained in the wettability test is a reservoir pH of the oil reservoir 175. For instance, results of the wettability test may be used to determine the optimum target injected water 160 (e.g., or a property thereof)

The control center 120 may then target the at least one optimized injection water metric by controlling the flow of the alteration water 140, in this exemplary case, by manipulation of a control valve 250. The produced water stream 210 and metered flow of alteration water 140 may then be mixed in a subsequent mixing station 220 to produce the actual injected water 160. A third at least one measurement device (not shown) may provide feedback control to the control center 230 to allow more accurate achievement of the optimum injected water target metric.

As is presently recognized, the at least one optimized injection water may be provided specifically for an oil reservoir of interest. The optimized injection water may be designed so as to alter a wettability of the oil reservoir to a favorable condition for oil recovery (e.g., a balanced water-wet/oil-wet condition). In this regard, it may be useful to accurately measure the wettability of the oil reservoir of interest and/or measure changes to the wettability of the oil reservoir of interest based on the introduction of an injected water having a particular property.

A number of methods of wettability measurement have been previously proposed. These proposed methods may measure the forces by observation of the macroscale behavior. Some are qualitative only methods; however several are quantitative. Table 1 provides a summary of a number of the proposed wettability measurement methods. The three quantitative methods most in use are the contact angle, Amott-Harvey and U.S. Bureau of Mines (USBM) test. The latter two of these methods involve measurement of fluid flow during spontaneous imbibition followed by forced displacement. Other macroscale methods include flotation, spontaneous imbibition, chromatographic separation, interfacial tension, optical methods (microscopic, FESEM), and capillary pressure.

TABLE 1

Wettability Measurement Techniques.

| Technique | Quant | Qual | Temp. | Res. Rock | Pressure | Res. pH |
|---|---|---|---|---|---|---|
| Amott-Harvey | X | | Y | Y | N | N |
| USBM | X | | N | Y | N | N |
| contact angle | X | | Y | N | Y | N |
| NMR | X | | Y | Y | Y | N |
| Chromatographic | X | | Y | Y | Y | N |
| Interfacial Tension | | X | Y | Y | N | N |
| Capillary Pressure | | X | Y | Y | N | N |
| Microscopic | | X | N | N | N | N |
| FESEM | | X | N | N | N | N |
| Modified Flotation | X | | Y | Y | Y | N |

Temp. refers to ability to usually make measurements at elevated T
Pressure refers to ability to make measurements at elevated P
Res. Rock refers to ability to measure actual rock surface rather than prepared surface
Res. pH refers to the restoration of reservoir pH during the measurement The indirect methods have wide acceptance, but significant limitations. One major limitation is that all the methods measure macroscale representations of the atomic-scale forces, which are the attractive van der Waals forces, the electrostatic forces which can be attractive or repulsive, and the steric forces. Another major limitation is the methods measure wettability on prepared systems, not the systems in the natural state. Lastly, the methods except for the Modified Flotation test are very difficult to apply to shale reservoirs.

Accordingly, proposed wettability measurements reflected in Table 1 have a distinct drawback in that measuring wettability in the natural state is not practical. While common procedural steps to mimic reservoir conditions may include controlling temperature, pressure and salinity, none of the wettability tests recognize the influence of pH on the wettability of a system. In turn, none of the wettability tests control for pH.

The rock utilized in such testing may be fresh core or restored. Fresh core means the sample was obtained using methods to attempt to preserve reservoir wettability. However, most tests are performed on restored core. Restored means the core is first cleaned to remove all oil and water. After cleaning the core is injected with brine and degassed oil to restore the relative amounts of each to those present in the reservoir. The oil-brine-rock system is then allowed to come to equilibrium at reservoir temperature and pressure, if technically feasible, before the measurement is made. Testing is typically performed with dead oil (e.g., degassed oil), reservoir rock and synthetic reservoir brine.

However and as described above, it is presently recognized that pH of a system affects wettability such that altering pH also alters the wettability of the system. As may be appreciated by a review of Table 1, no current wettability measurement techniques try to restore reservoir pH, meaning no current measurements can produce accurate wettability values that match in-situ reservoir conditions. As a result, wettability tests that do not control for pH may present inaccurate results that do not reflect actual oil reservoir behavior including effects of attempted modifications to the wettability of the oil reservoir.

Figure 3:
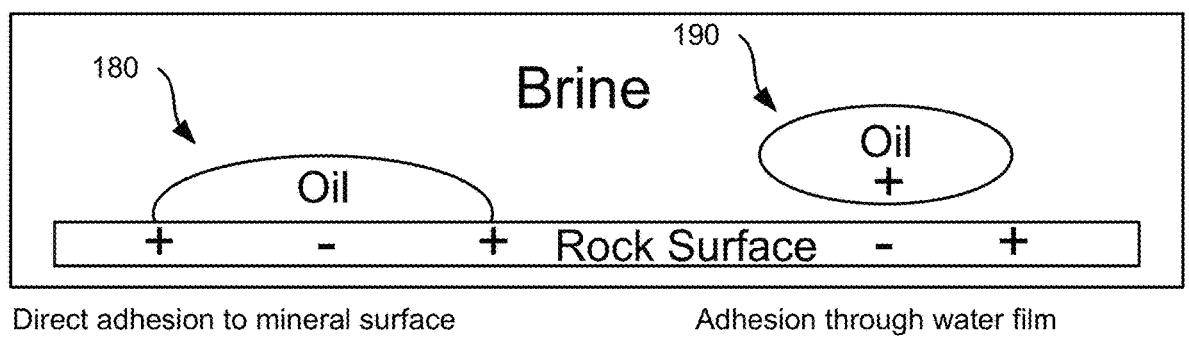
FIG. 3 illustrates adhesion of oil in-situ through direct contact with a mineral surface and via adhesion through a water film.

In turn, the present disclosure recognizes the applicability of pH to wettability. Specifically, as described above, it is recognized that polar portions of the oil interact with surface charges present in the reservoir. This drives portions of the reservoir being oil-wet or water-wet depending on the specific chemistries present in-situ. Such interaction may be present where oil is in contact with the surface 180 or separated by a water film 190 as shown in FIG. 3. These chemical reactions that cause attraction between the polar elements in the oil and the mineral surface can be described with a set of reversible chemical reactions.

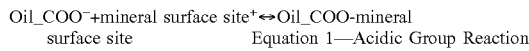

Equation 1—Acidic Group Reaction

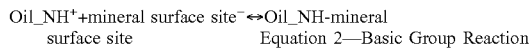

Equation 2—Basic Group Reaction

The fundamental outcome of this model is that current measurement methods cannot separate the contribution of the two modes to the measured wettability. Moreover, this approach fails to contemplate the complexity of conditions in-situ. As described above, it is presently recognized that the in-situ pH of a reservoir is a major driver in the wettability of the reservoir.

Figure 5:
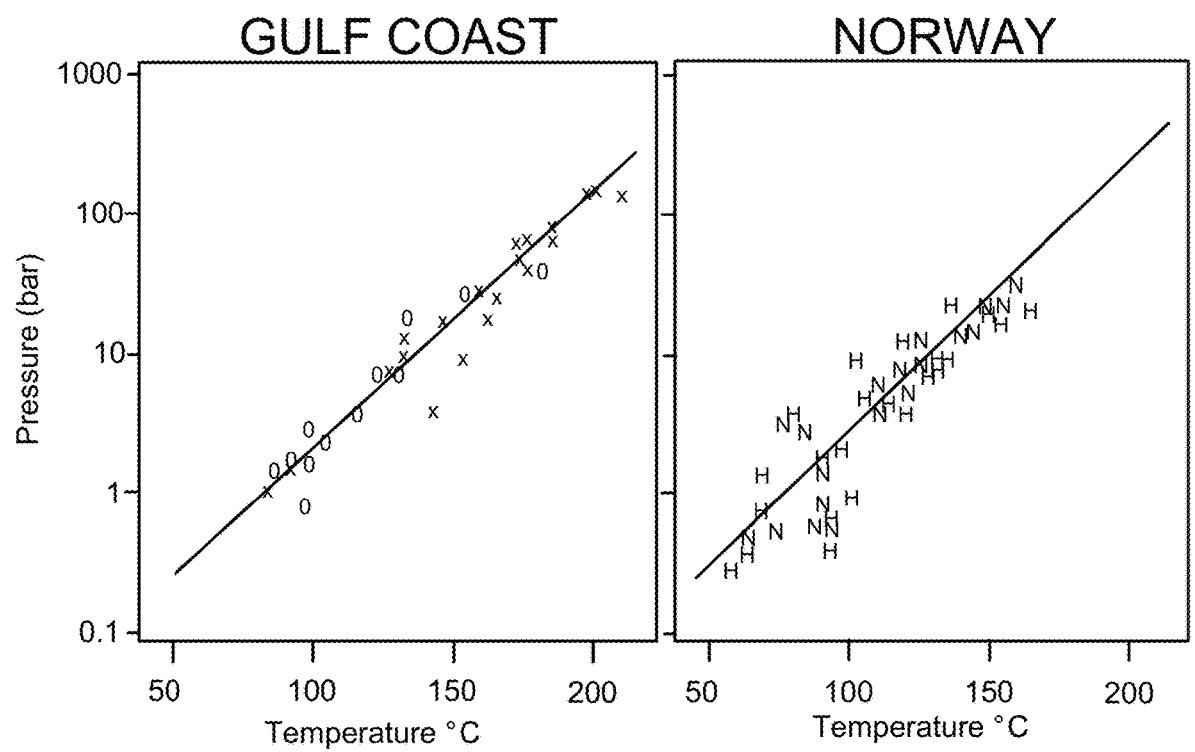
FIG. 5 illustrates partial pressure of carbon dioxide (in bars) versus temperature for two exemplary oil reservoirs.

Oil reservoirs typically have pH values between 4.5 and 7. It has been observed that the pH in most reservoirs is controlled by the interaction of feldspar and clay minerals with the brine at temperatures above 50° C. The chemical equilibrium of the mineral-brine reactions are dependent on temperature with the result that pH of the reservoir brine decreases as temperature increases. The reservoir pH can be calculated by geochemical modeling based on reservoir mineralogy and brine composition. Deeper and hotter reservoirs have more acidic pH values compared to shallower and cooler reservoirs. This is illustrated in FIG. 5, which shows two plots of exemplary oil reservoirs in which temperature is plotted against a pH proxy, $pCO_2$, with $pCO_2$ on the vertical axis and temperature on the horizontal axis.

Almost all reservoirs have some amount of carbonate minerals such as calcite, dolomite or siderite. The brine pH sets the carbonate mineral equilibrium including controlling the dissolved carbonate content so that the dissolved carbonate increases as pH decreases (becomes more acidic). The dissolved inorganic carbon content produced is sometimes represented as the partial pressure of carbon dioxide ($pCO_2$). If the gas content of the reservoir gas cap is known together with the composition of the brine, the pH of the reservoir can be calculated using Henry's Law. Henry's Law describes the distribution between pressure of a gas and the amount of dissolved gas. The $pCO_2$ value can be converted to reservoir pH using the Henry' Law coefficient appropriately modified for the effect of pressure and temperature.

With returned reference to the effect of pH in the oil reservoir on wettability, if the mineral surface charge is primarily negative and the oil is positive then there is significant potential for attraction between oil and mineral surface enabling oil wetting (adhesion). Clay minerals have a negative surface charge at reservoir pH values of 4.5 to 7. Acidic polar groups of oil are either neutral or negatively-charged and therefore have little or no adhesion with negatively-charged surfaces. This situation promotes water wetting. However, if the reservoir pH is decreased to 5.5 or less, most of the basic polar groups are positively-charged and potentially attracted to the negatively-charged surfaces favoring adhesion and promoting oil wetting.

Carbonate mineral surfaces have both positive and negative surface sites over the in-situ reservoir pH range. At lower pH values in deeper hotter reservoirs (<5.5), the sum of carbonate mineral sites is slightly positive (more positive than negative sites), but shifts to more negative values as pH values increase. So in the carbonate portion of sandstones or shales, or in carbonate reservoirs with lower pH values, we would expect the base components in crude oil to promote oil wetting by interacting with the negatively-charged surface sites, but not the positively-charged sites.

The organic acids and bases in oil are composed of many organic compounds, but for computation purposes, the system may be simplified by assuming that all organic acids have a neutral charge point (pKa) at pH of 6. This means that half of the acid is protonated (Oil_COOH) and half is deprotonated (Oil_COO$^-$) at a pH value of 6. The same is true of the organic bases in that while there are many specific organic compounds we will represent them with a single value where the neutral charge point (pKb) for the organic bases is around 5, so half the base is uncharged (Oil_N) and half is charged (Oil_NH$^+$) at pH values of 5. This general model can be modified if more detailed characterization of the polar components is available.

The general chemical reactions for the oil are expressed as:

Eq. 3—Acid Reaction

Eq. 4—Base Reaction

Similar reactions can be developed for the surface complexation models for reservoir minerals such as clays and carbonates. In addition, chemical reactions for the various ions in the reservoir brine and minerals and mineral surfaces may be provided. These reactions are well understood and equilibrium constants for the chemical reactions are readily available. Combined with the generalized reactions for the oil, standard surface complexation models (SCM) may be modified to simulate oil wetting. However, these current models do not have equilibrium constants for the reactions shown in Equations 1 and 2 provided above. Rather, current models use arbitrary values that only predict the wettability trends rather than quantitative results. Attempts to estimate the apparent equilibrium constants by fitting to laboratory data have limited results as the existing data is not sufficient to fully constrain the calculation because reservoir wettability depends on reservoir pH which is not reproduced in the experiments.

Figure 4:
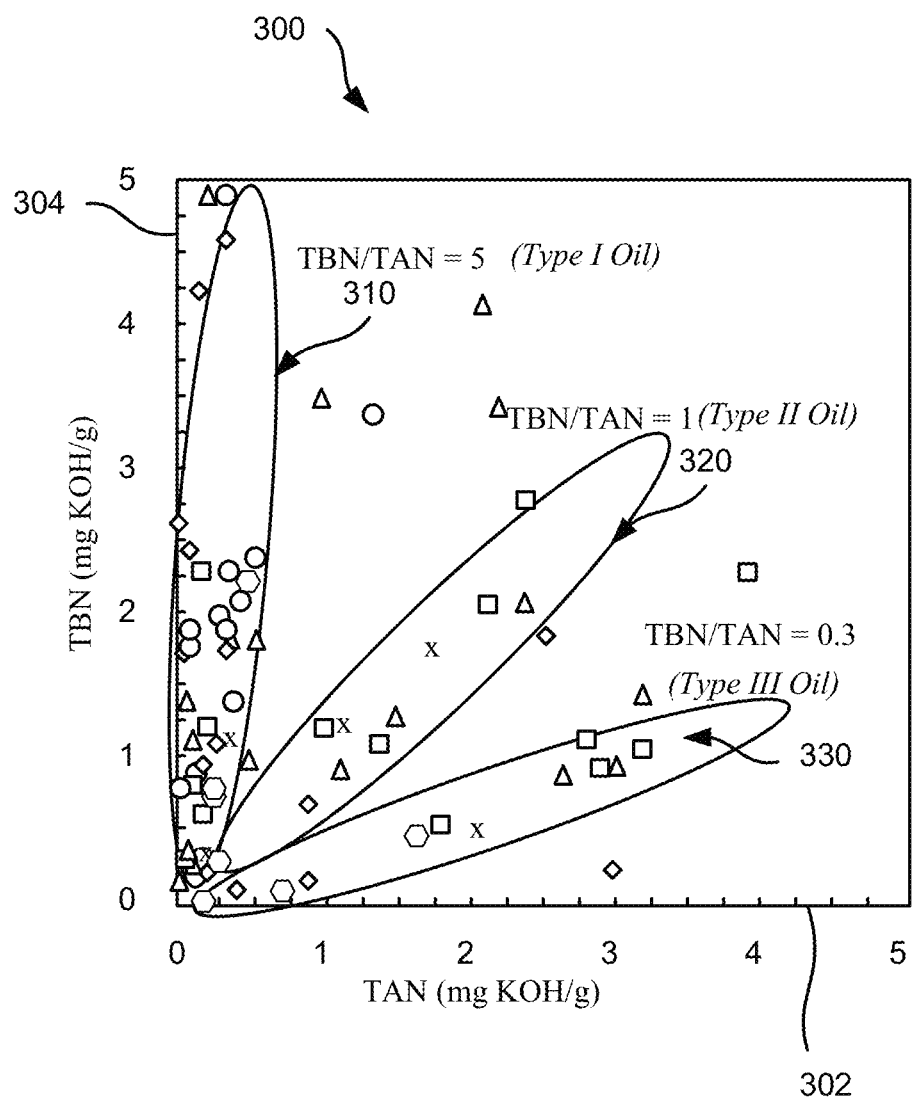
FIG. 4 illustrates a plot of total acids versus total base for crude oil samples.

Moreover, it is currently recognized that the effect of pH in an oil reservoir may vary for different oil types. Specifically, the ratio of polar acid to base groups in the oil is important to consider. This factor is not considered in current experiments, models or wettability measurement techniques. The most common measure of acids and bases in oil are the total acid and base numbers, TAN and TBN, respectively. The acid and base content of crude oils is shown in plot 300 of FIG. 4. Each plot point represents a different oil sample plotted relative to TAN on the horizontal axis 302 and TBN on the vertical axis 304. The data shows that most crude oil falls into one of three groups based on the base to acid ratio. These three types of oils are base-rich (Type I) 310, neutral (Type II) 320, and acid-rich (Type III) 330. The majority of oil samples fall into the base-rich oil (Type I) 310 (which may have an approximate ratio of TBN/TAN=5). The Type II oil 320 has an approximate 1:1 base to acid ratio (TBN/TAN=1), while the acid-rich oil (Type III) 330 may have a ratio of approximately 0.3 (TBN/TAN).

We can see from the Equations 3 and 4 above that the pH of the brine directly controls the speciation of the acids and bases. However, the effect at specific pH values could be quite different depending on oil type. Accordingly, while wettability experiments or tests that do not control pH may be somewhat predictive of some of the oil represented in FIG. 4, accurate testing cannot be achieved for all oil types without control of experimental pH. To illustrate this consider a shale or sandstone reservoir at pH 5 with Type 1 oil. The base component, which is 5 times more than the acid component, gives the oil surface an overall positive charge. Since the clay surfaces in the sandstone or shale are negatively-charged, Type 1 oil is likely to wet those mineral surfaces making that portion of the reservoir oil-wet. In contrast, in the same situation with Type 3 oil where the acids outnumber bases by 3 to 1, the polar content of the oil is mostly neutral producing little attraction and promoting water wetting.

It is presently recognized that accurate wettability measurement requires restoration of pH to in-situ reservoir conditions. All current methods allow the pH of the measurement to be set by the experimental conditions rather than by controlling the experimental pH to replicate reservoir pH. This means the pH of the currently available wettability measurements will be between 7 and 9 with the control of pH determined by the mineral assemblage, brine with dissolved gas and oil compositions. Most reservoir mineral assemblages will contain carbonate minerals. The synthetic brines that together with atmospheric $CO_2$ content will produce a pH value between 7 and 9. None of the current methods purposefully match experimental pH and reservoir pH. Examination of equations for mineral surface and oil charge show that both surface charge and oil charge may be significantly different at laboratory conditions compared to reservoir conditions.

Consider the example discussed in the section above. In the Type 1 oil example, the sandstone or shale reservoirs is likely to be oil-wet at in-situ reservoir pH of 5 since most of the charge on the oil is positive and most of the charge on the reservoir is negative. However, if the wettability is measured at laboratory conditions where the pH has increased to above 7 due to the environmental conditions such as the lack of the same dissolved gases found in the reservoir, especially $CO_2$. In the laboratory at pH values above 7, the major contributor to the oil polarity (charge) is the negatively-charged acids whereas all the bases are neutral. The negatively-charged oil and minerals will repulse each other creating a water-wet condition during laboratory measurement—the opposite of the actual conditions in the reservoir.

Flotation in both qualitative and quantitative modes has been proposed with model and natural oils, synthetic brine and reservoir rock to characterize wettability at laboratory pH without considering the effect of pH on the wettability of the system. The traditional technique uses the following basic steps 1) rock powder is wet with reservoir brine (synthetic), 2) the oil is added and mixed with the wet rock, 3) the system is allowed to equilibrate, and 4) more brine is added to the system to separate the water-wet and oil-wet rock, 5) the oil-wet rock is extracted and the remaining water-wet rock is dried and weighted to determine the relative fractions. This method produces quantitative measurement of wettability.

Figure 6:
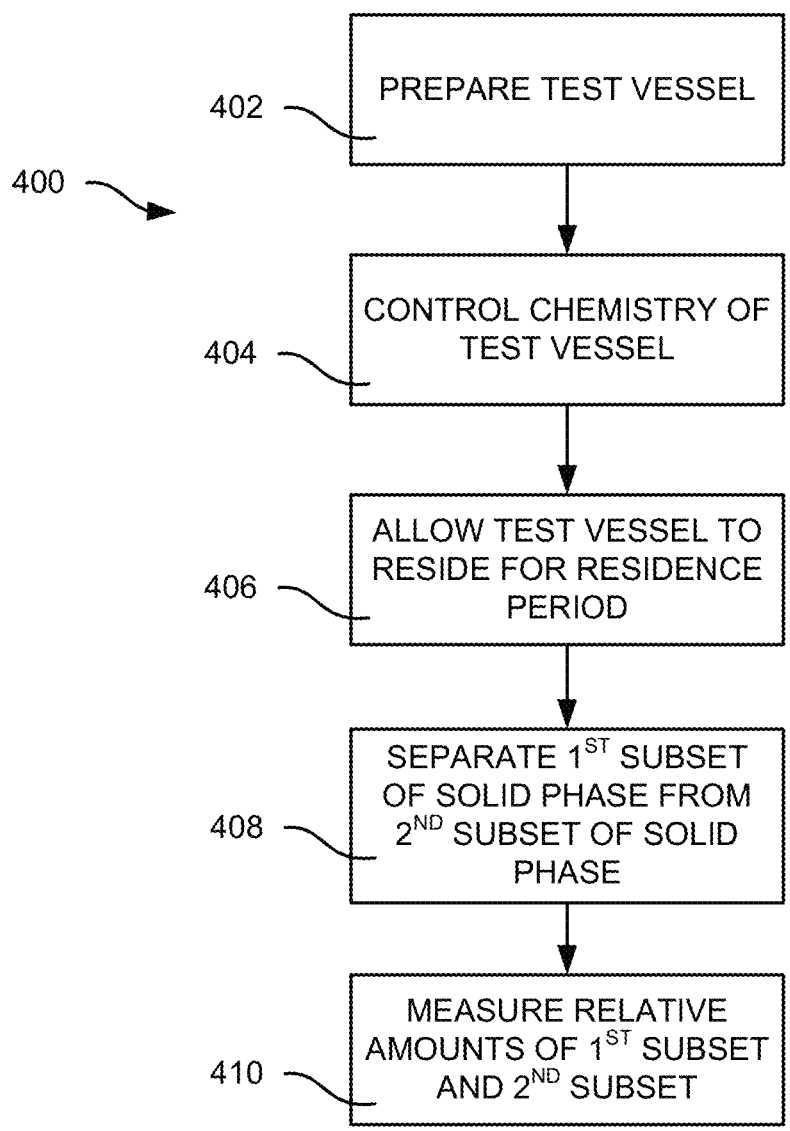
FIG. 6 illustrates an example of a method for performing a modified floatation test with replicated is-situ reservoir conditions.

FIG. 6 depicts an example of a method 400 for performing a modified flotation test of a system that corresponds to an oil reservoir of interest. The method generally includes preparing 402 a test vessel that contains a number of samples. Specifically, the test vessel may include a solid phase sample, an aqueous phase sample, a gas phase sample, and an oil sample. In turn, the method may include controlling 404 a chemistry of the test vessel to achieve a desired experimental pH. As described in greater detail below, this may include establishing a temperature and $pCO_2$ approximating the oil reservoir of interest and/or may include pH modifying additives such as mineral acid (e.g., nitric acid or hydrochloric acid). In any regard, the experimental pH may correspond to the conditions in the oil reservoir of interest. As described above, the pH of the oil reservoir of interest may be determined based on application of Henry's Law to a given oil reservoir of interest. In addition, the controlling of the chemistry of the test vessel may include maintaining the test vessel at a reservoir temperature and pressure. Furthermore, controlling the test vessel may include establishing a partial pressure of $CO_2$ in the test vessel such that the experimental pH of the test vessel approaches, if not reaches, the pH of the reservoir of interest.

In this regard, the test vessel may be located in an oven or other means for controlling the temperature of the test vessel. Moreover, the test vessel may be in fluid communication with a high-pressure gas phase source. The gas phase source may comprise a $CO_2$ source. Alternatively, the gas phase may be another gas that may contain $CO_2$ as a constituent component. In any regard, control of the test vessel may include establishing a pressure within the test vessel so as to establish a partial pressure of $CO_2$ to mimic the reservoir conditions (e.g., such that the experimental pH approximates the reservoir pH)

Once the test vessel containing the various samples achieves reservoir conditions including an experimental pH within the test vessel that mimics that of the reservoir pH, the test vessel may be allowed to reside 406 for a residence time period. The residence time period may be sufficient such that the contents of the test vessel approach an equilibrium. In this regard, the test vessel may, but need not, come to equilibrium at the conclusion of the residence time period.

As may be appreciated, at the conclusion of the residence time period, the solid phase sample in the test vessel may exhibit an affinity for either the aqueous phase sample or the oil sample. In this regard, a first subset of the solid phase sample may be in the aqueous phase sample and a second subset of the solid phase sample may be in the oil sample. The relative amounts of solid phase sample in each of the aqueous phase and the oil phase may be indicative of the wettability of the system corresponding to the contents of the test vessel.

As such, the method may include separating 408 the first subset of sold phase sample particles from the second subset of solid phase sample particles. The relative amounts of the first subset and the second subset of solid phase particles may be measured 410 to determine a wettability of the system. Optionally, the wettability of the system may be expressed in relation to a wettability index such as, for example, an Amott index.

The modified float test shown in FIG. 6 may provide distinct advantages as the system contained by the test vessel may be exposed to experimental conditions approximating or replicating reservoir conditions. Thus, the wettability determination from the modified floatation test 400 may provide a more accurate representation of actual conditions with the oil reservoir of interest.

Figure 7:
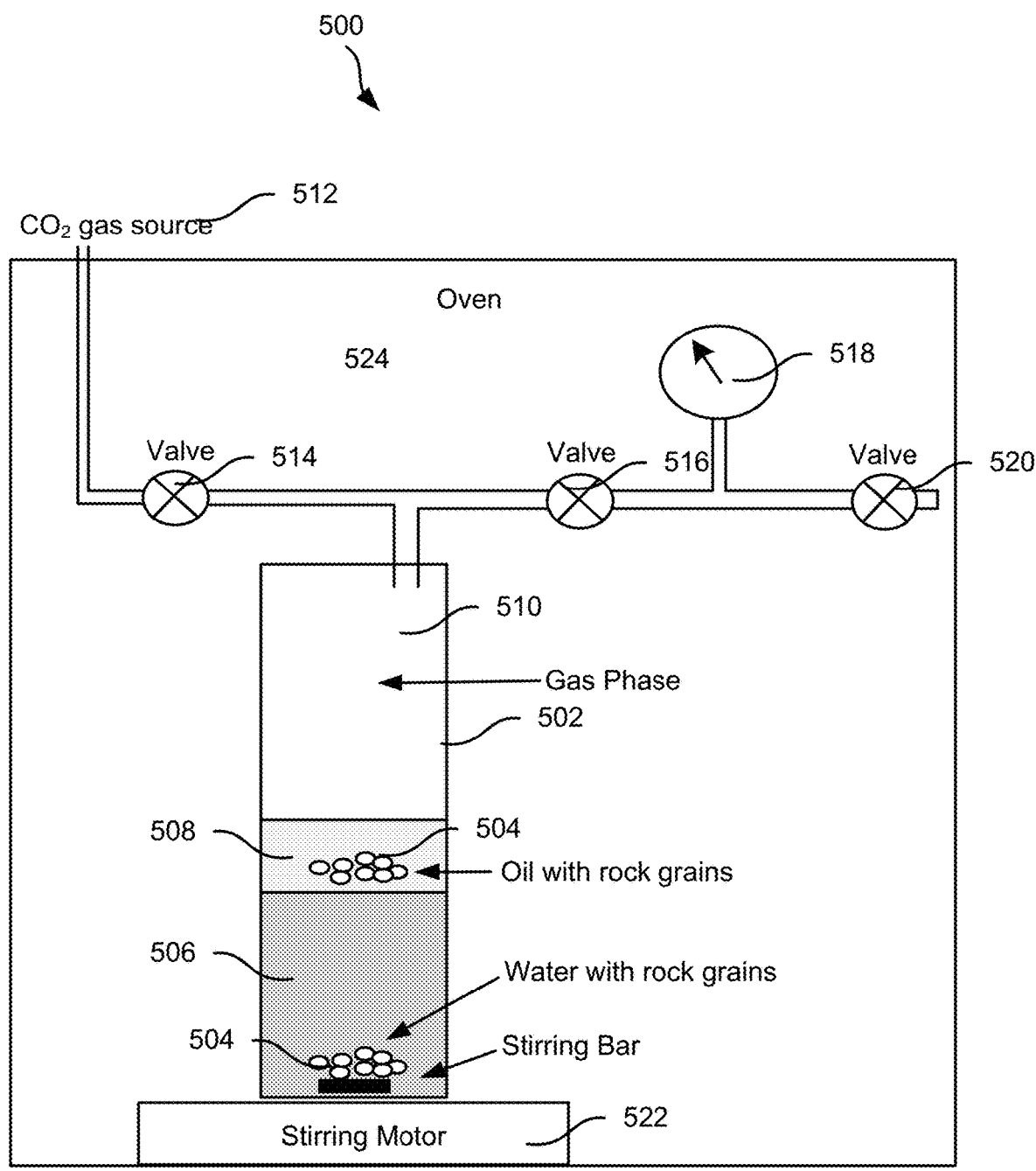
FIG. 7 depicts an example of a testing apparatus according to the present disclosure.

FIG. 7 shows a schematic representation of a laboratory setup 500 that may facilitate the modified flotation test (e.g., the method 400). The respective samples provided in the test vessel 502 may be particularly chosen in view of the oil reservoir to provide a replication of the conditions in the oil reservoir. For instance, the relative volumes of the solid phase sample 504, aqueous phase sample 506, gas phase sample 510, and the oil sample 508 may be provided in the test vessel in a volumetric ratio approximating a relative ratio of reservoir rock, reservoir formation water, gas phase, and oil in the reservoir of interest. By approximating, it is meant that the volumetric ratio approaches that of the reservoir of interest such that, for example, the ratio is within +/−10% of the actual volumetric ratio of the oil reservation, within +/−5% of the actual volumetric ratio of the oil reservation, or even within +/−2% of the actual volumetric ratio of the oil reservation. In one particular example, the solid phase sample 504, the aqueous phase sample 506, the oil sample 508, and the gas phase sample 510 may be provided in the test vessel 502 at a volumetric ratio of about 1:10:3:20.

The solid phase sample 504 may comprise reservoir rock corresponding to the oil reservoir of interest. While the solid phase sample 504 may comprise reservoir rock obtained directly from the oil reservoir of interest, a solid phase sample 504 comprising reservoir rock from a similar reservoir may also be used. By similar reservoir it may mean that the relative mineral content may approximate the actual reservoir of interest. The reservoir of interest may comprise at least one of a sandstone, limestone, dolomite, chalk, chert, carbonate, another oil bearing geological media, or a combination thereof. Moreover, it is noted that the modified flotation test described herein is specifically contemplated for use with shales. In addition, while the solid phase sample 504 is shown in FIG. 7 as being separated, it may be appreciated that this may depict some period after addition of the solid phase sample 504. Thus, the solid phase sample 504 may be added to the test vessel 502 in a single addition.

In any regard, the solid phase sample 504 may be prepared prior to being added to the test vessel 502. This may include physically sizing the solid phase sample 504. Preferably, the reservoir rock may be provided in a sufficiently small granular form such that the surface forces are allowed to dominate the wettability of the system. In this regard, the reservoir rock may be provided in a sufficiently small granular form such that gravitational forces that cause the rock to sink in the test vessel may be counteracted by the surface forces between the oil and rock surface acting on the reservoir rock particles. As may be appreciated, this may be at least in part based on the density of the reservoir rock. In turn, an appropriate calculation or look-up chart may be employed to select the size of the particles of reservoir rock to allow surface forces to dominate rather than gravitational or other forces. This may include grinding the reservoir rock into a fine powder. Most reservoir minerals have a grain density between 2.2 and 2.8 grams per cubic centimeter. Therefore, grains with a diameter greater than 1000 microns (1 mm) will sink regardless of adhesion between the grains and oil. For instance, the reservoir rock may be ground into particles having a mean diameter of no greater than 500 microns, 250 microns, 100 microns, or even 50 microns.

The aqueous phase sample 506 may also correspond to a reservoir formation water found in the oil reservoir of interest. For instance, the aqueous phase sample 506 may comprise a produced water that is obtained directly from the oil reservoir of interest. In this regard, the in-situ wettability of the oil reservoir of interest may be determined using the test described herein where the aqueous phase sample 506 is directly obtained from the oil reservoir of interest.

Additionally, an aqueous phase sample 506 may be specifically altered to provide additional information regarding the effect of a modified or synthesized water that is introduced into the oil reservoir of interest. As may be appreciated, this additional information may be used in connection with designing a synthesized water to be introduced into the oil reservoir of interest in connection with an oil recovery process. As will be described in greater detail below, different aqueous phase samples 506 be used in a plurality of test vessels to provide the additional information regarding the effect of the different respective aqueous phase samples 506 on the wettability of the oil reservoir of interest.

The oil sample 508 may comprise an oil obtained directly from the oil reservoir of interest. In this regard, the oil sample 508 may comprise crude oil obtained from the oil reservoir of interest. Alternatively, the oil sample 508 may comprise an extract of crude oil (e.g., a liquid extract of the oil). In any regard, the oil sample 508 should exhibit similar chemical characteristics to the oil in the oil reservoir of interest for determination of accurate wettability values associated with the oil reservoir of interest. In this regard, the oil sample 508 may comprise a synthesized oil sample having at least one property in common with the oil reservoir of interest (e.g., including a TAN and/or TBN).

The gas phase 510 may also be selected to replicate conditions in the oil reservoir of interest. In this regard, the components of the gas phase 510 may be selected to mimic or replicate a gas present of the oil reservoir of interest. Alternatively, a gas phase 510 with a different composition may be selected, with specific characteristics that drive replication of conditions in the oil reservoir of interest. For instance, the gas phase 510 may comprise atmospheric air such that the gas phase 510 comprises, among other potential components, nitrogen, oxygen, argon, and carbon dioxide. In this regard, the gas phase 510 may be controlled to mimic certain properties of the gas phase of the oil reservoir of interest. For instance, as described above, the partial pressure of $CO_2$ in the test vessel 502 may be a primary driver of the pH of the system contained within the test vessel 502. In this regard, the vessel partial pressure of carbon dioxide may be controlled to mimic or replicate the partial pressure of $CO_2$ in a gas phase 510 of the oil reservoir of interest. In this regard, the gas phase 510 in the test vessel 502 may be maintained at a pressure of not less than about 10 psi. Alternatively, the test vessel 502 may be maintained at a pressure of not less than about atmospheric pressure. The maximum pressure of the test vessel 502 may not exceed a maximum pressure in the reservoir of interest (e.g., which may be measured or calculated). Moreover, the maximum pressure in the test vessel 502 may not exceed a maximum hydrostatic pressure gradient of the system in the test vessel.

The control of pressure is essential as the addition of acid to the system in the form of pH-adjusted brine will cause dissolution of carbonates and generation of $CO_2$ gas until equilibrium is reached. In this regard, a gas phase source 512 may be provided in fluid communication with the test vessel 502. The gas phase source 512 may comprise a high-pressure $CO_2$ gas source. A supply valve 514 is located between the gas phase source 512 and the test vessel 502 to control flow of the gas phase 510 from the gas phase source 512 into the test vessel 502. A gauge valve 516 may be disposed between the test vessel 502 and a pressure gauge 518 to allow for monitoring of the pressure of the test vessel 502. Additionally, a vent valve 520 may be provided to release the pressure in the test vessel 502.

The $pCO_2$ may reach pressures of 10+ atmospheres for some cases (as reflected in the plots of FIG. 5). Rather than allow significant dissolution of the rock it is desirable to maintain the $CO_2$ pressure by adding appropriate amounts to the gas phase after adding the brine back into the oil-wet rock system.

The system may then be stirred using a mixer 522 (e.g., a mixing bar and stirring motor) and allowed to reside for a period or equilibrate before removing the oil-wet (floating) portion of the rock. This technique also avoids the problems that the traditional techniques have in low permeability rocks such as tight sandstones and shales.

Additionally, the test vessel 502 may be located within an oven 524. The oven 524 may be used to control the temperature of the test vessel 502 during the test. In this regard, the oven 524 may be used to control the temperature of the test vessel 502 to replicate a temperature of the oil reservoir of interest.

Figure 8:
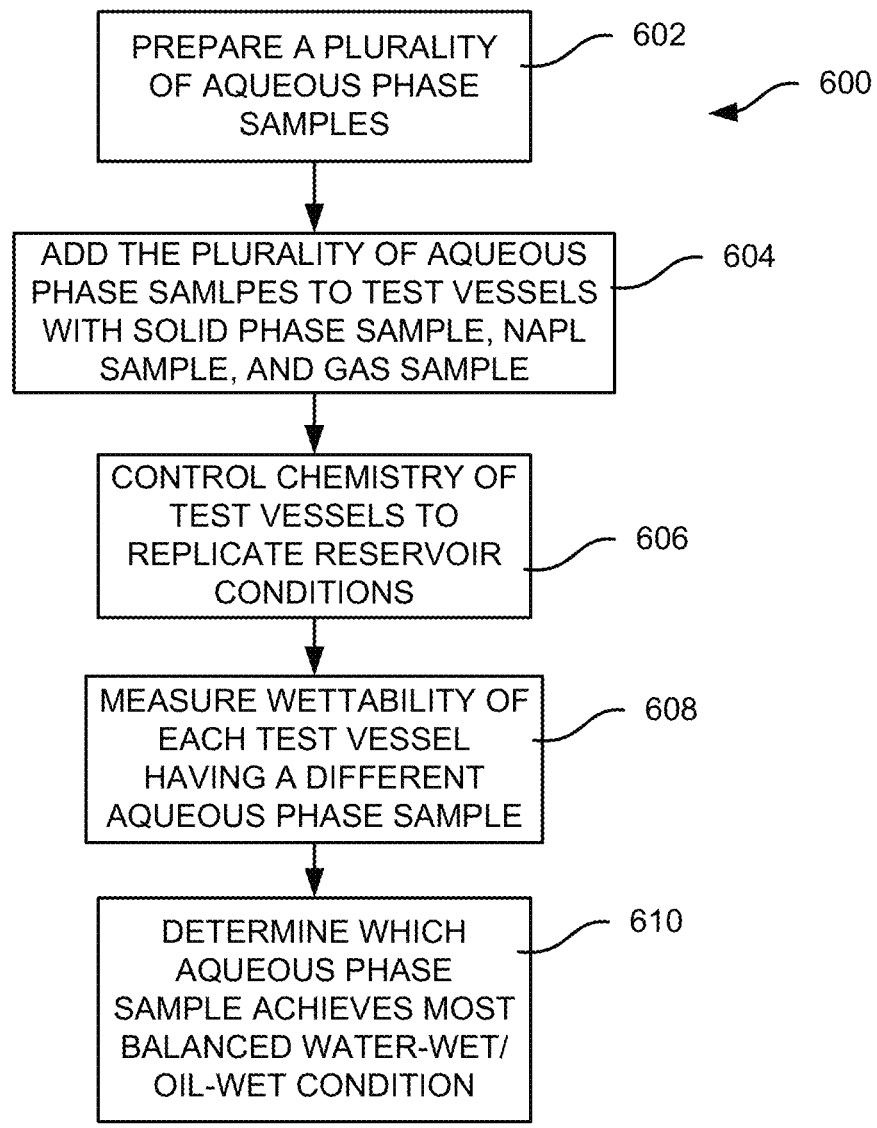
FIG. 8 illustrates an example of a method for performing a modified floatation test with replicated in-situ reservoir conditions for empirical determination of an optimized injected water.

In relation to use of varying aqueous phase samples 506 to derive information regarding modification of an oil reservoir with injected water, an empirical approach and a model-based approach are contemplated to derive this additional information on the effect of the aqueous phase sample on the wettability of the system. The empirical approach is descried in relation to FIG. 8, which depicts an example of a method 600 embodying the empirical approach. The method 600 may include preparing 602 a plurality of different aqueous phase samples that each differ with respect to at least one chemical characteristic. In turn, the different aqueous phase samples may be added 604 to different test vessels also containing the solid phase sample, the oil sample, and the gas phase sample. For instance, each different aqueous phase sample may comprise a produced water corresponding to the reservoir of interest mixed with a second water to alter the at least one chemical characteristic of each sample. The method 600 may include controlling 606 the chemistry of each test vessel to replicate reservoir conditions as described above. In turn, the method 600 may include measuring 608 the wettability of each respective system determined to provide information on the effect of the at least one chemical characteristic of the aqueous phase sample on the wettability of the oil reservoir. In an example, the chemical characteristic that is varied across the various aqueous phase samples may comprise an amount of TDS. In this regard, the amount of TDS in the aqueous phase sample may be greater or less than the amount of TDS in the aqueous phase of the oil reservoir of interest. Accordingly, the method 600 may include determining 610 which of the aqueous samples provide favorable modifications to reservoir wettability. Specifically, it has been found that oil production may be maximized when a reservoir is as water-wet as it is oil-wet. In this regard, the determining 610 may include identifying which of the aqueous phase samples achieves the most balanced water-wet/oil-wet system. In turn, the identified aqueous phase sample that achieves the most balanced wettability may be targeted as corresponding to an injected water to be used in connection with the reservoir of interest.

Figure 9:
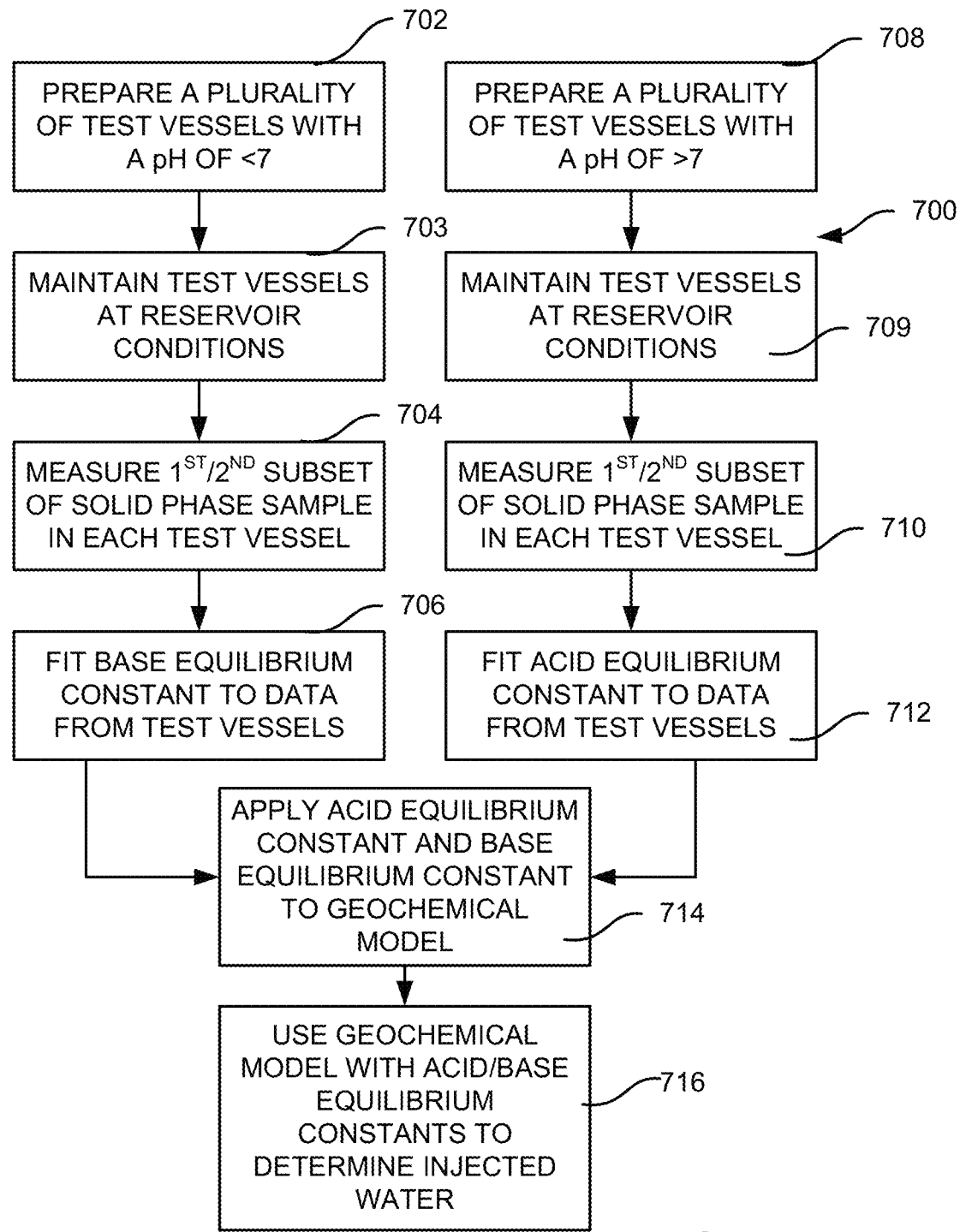
FIG. 9 illustrates an example of a method for determining equilibrium constants related to a geochemical model of an oil reservoir.

An example of a method 700 associated with a model-based approach is depicted in FIG. 9. In such an approach, different test vessels comprising different chemical properties may be used to derive equilibrium constants for a geochemical model of the reservoir of interest. Specifically, in the model-based approach, the method 700 may include preparing 702 a plurality of test vessels that are acidic. The preparing 702 may include calculating the formation water chemistry from the formation water analysis correcting for any changes due to mineral precipitation (scaling) and other changes caused by alteration of temperature and pressure during production and sampling. The preparing 702 may include calculating the reservoir pH. In turn, the preparing 702 may also include formulating the correct synthetic reservoir brine for use in the flotation experiment. The method 700 may also include maintaining 703 the test vessels at reservoir conditions. The maintaining 703 may include adjusting the experimental pH and temperature to the reservoir value to determine in-situ reservoir wettability. This may include maintaining the test vessels at a reservoir pH. As described above, control of pH can be applied by either or both controlling the pH in the brine by adjustment using mineral acids (nitric, hydrochloric, etc.) and bases (sodium hydroxide, etc.) or by controlling the $CO_2$ content of the gas phase. The method 700 may also include measuring 704 the first subset and second subset of solid phase sample in the aqueous phase sample and oil sample as described above. In turn, the method 700 may include fitting 706 a base equilibrium constant based on the results of the wettability test resulting from the measuring 704. In this regard, the acidic test vessels may result in isolation of the base component's contribution to wettability in the system. Hence, the base equilibrium value may be determined from testing of acidic test vessels. That is, the acidic test vessels may have a pH of less than 5, less than 4, or even less than 3. Accordingly, the wettability may be repeated in the acidic test vessels to derive the data to determine the contribution from the base components of the oil to wettability and the equilibrium constant for basic polar component of oil.

The method 700 may also include preparing 708 a plurality of test vessels that are basic. The preparing 708 may utilizing (from the preparing 702) or calculating the formation water chemistry from the formation water analysis correcting for any changes due to mineral precipitation (scaling) and other changes caused by alteration of temperature and pressure during production and sampling. The preparing 708 may include utilizing (from preparing 702) or calculating the in-situ reservoir pH. In turn, the preparing 708 may also include formulating the correct synthetic reservoir brine for use in the flotation experiment. The method 700 may also include maintaining 709 the test vessels at reservoir conditions in a manner as described above. The method 700 may also include measuring 710 the first subset and second subset of solid phase sample in the aqueous phase sample and oil sample as described above. In turn, the method 700 may include fitting 712 an acid equilibrium constant based on the results of the wettability test resulting from the measuring 704. In this regard, the basic test vessels may result in isolation of the acid component's contribution to wettability in the system. Hence, the acid equilibrium value may be determined from testing of basic test vessels. For instance, the basic test vessels may have a pH greater than 7, greater than 8, or even greater than 9. Accordingly, the wettability may be repeated in the basic test vessels to derive the data to determine the contribution from the acid components of the oil to wettability and the equilibrium constant for acidic polar component of oil.

In relation to the fitting steps 706 and 712, electrostatic interactions acting through a water film in oil wetting can be described using standard surface complexation models that include chemical reactions describing the mineral and oil surface charges. To date the only efforts have been limited to fitting experimental data to determine an acid component equilibrium constant, however the experimental data was not complete resulting in a non-unique value. Chemical equilibrium constants can be determined from experimental data using graphic methods, curve fitting or optimization codes. However, it is much easier to use an automated parameterization code for the same purpose linked to a geochemical code. These geochemical codes will speciate aqueous solutions, simulate aqueous equilibria with solid phases and gases as well as reactions between the mineral surfaces and aqueous species or other surfaces such as oil surfaces. Rigorous application of this method requires a complete chemical description of the experimental system. This includes the chemistry and pH of the brine and the reactive surface area of the rock particles in the system. If this data is available for several salinity values where the only change in the system is the salinity and resulting wettability, then the value for the equilibrium constant can be solved by fitting. This procedure requires that all the wettability be attributed to a single chemical reaction such as Equation 1 for the acid components and Equation 2 for the base components of the oil.

In the case of the flotation experiments this means:
1—analysis of the brine chemistry after a residence period or equilibration,
2—pH value of the experimental system,
3—measurement of the wettability of the laboratory system,
4—data from several wettability experiments with different salinities.

In this approach the surface area is treated as a variable parameter in the geochemical model within known limits at the start of the automated parameterization. The initial values for surface area are assumed based on volume percentage and the geometric surface area (specific surface). Surface roughness or the difference between actual reactive surface area and the equivalent geometric surface area (assuming a smooth surface) places limits on the range of values allowed during fitting. For natural samples, the average roughness may range from 7 to 2600, but is usually much less providing initial bounds on the value during iteration. The number of reactive sites per unit surface area of the minerals is also a fitting parameter. For carbonates, previous work has suggested 5 sites/nm$^2$, however, this parameter has been varied to 2 sites/nm$^2$ for fitting to experimental data.

As such, an acid equilibrium constant may be derived and a base equilibrium constant may be derived. The acid equilibrium constant may provide an equilibrium constant associated with Equation 1 above in the geochemical model. The base equilibrium constant may provide an equilibrium constant associated with Equation 2 above in the geochemical model. In turn, the method 700 may include applying 714 the acid and base equilibrium constants to a geochemical model. In turn, the geochemical model may be used 716 to determine an optimal synthesized water for use in oil recovery. As described above, the synthesized water may comprise produced water mixed with a second water to achieve the injection water used in the oil recovery operations.

Figure 10:
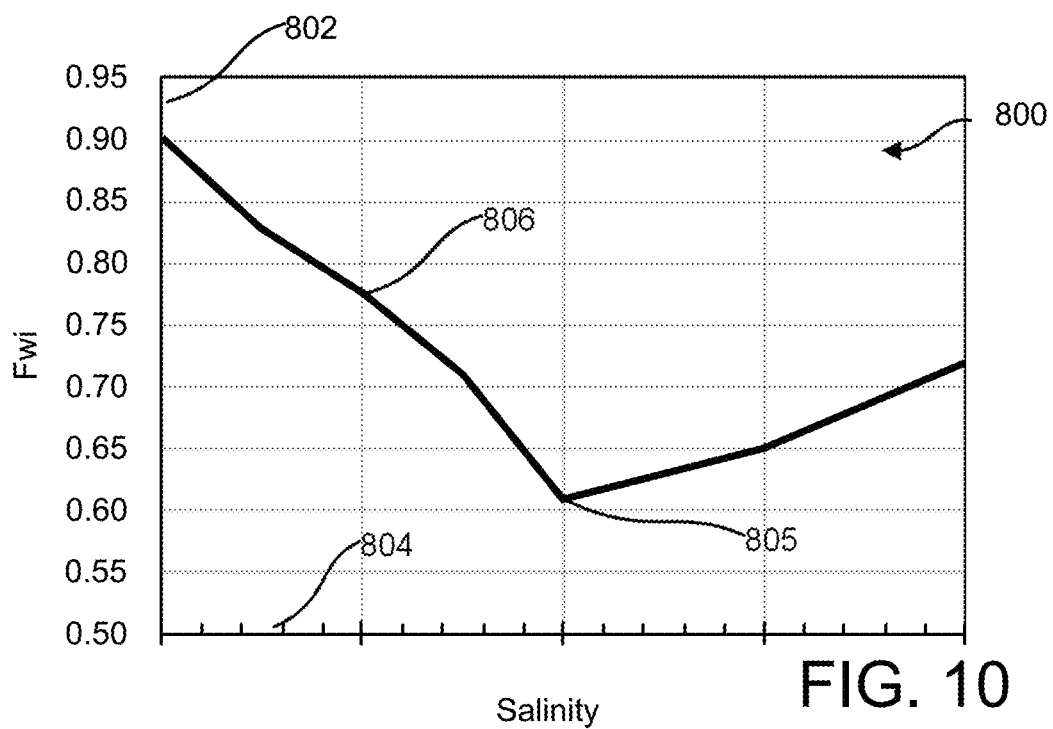
FIGS. 10-11 illustrate example results for wettability testing in which salinity is varied over a number of samples.

With further reference to FIG. 10, a plot 800 of results 806 for a number of wettability tests according to the present disclosure is presented. The vertical axis 802 represents wettability with respect to either one of water or oil. As may be appreciated, the wettability scale may be represented either as the percentage the system is water wet or the percentage the system is oil wet, understanding that each measure may be the other's inverse (e.g., a 30% water wet system may be a 70% oil wet system). The horizontal axis 804 represents the salinity of the aqueous phase in a test system. In this regard, a number of tests may be conducted with aqueous phases with different salinities to produce the results 806 plotted in FIG. 10. As may be appreciated, the wettability of the test system may decrease to a minimum at an inflection point 805. In turn, increased salinity beyond this point causes the system to increase in wettability. In this regard, the inflection point 805 may correspond with a salinity of the aqueous phase in which wettability of the system for recovery of oil is maximized. As may be appreciated, the inflection point 805 represents the value of the test system in which the wettability approaches the most balanced point (e.g., result with the closest wettability of 50% water wet, 50% oil wet).

Figure 11:
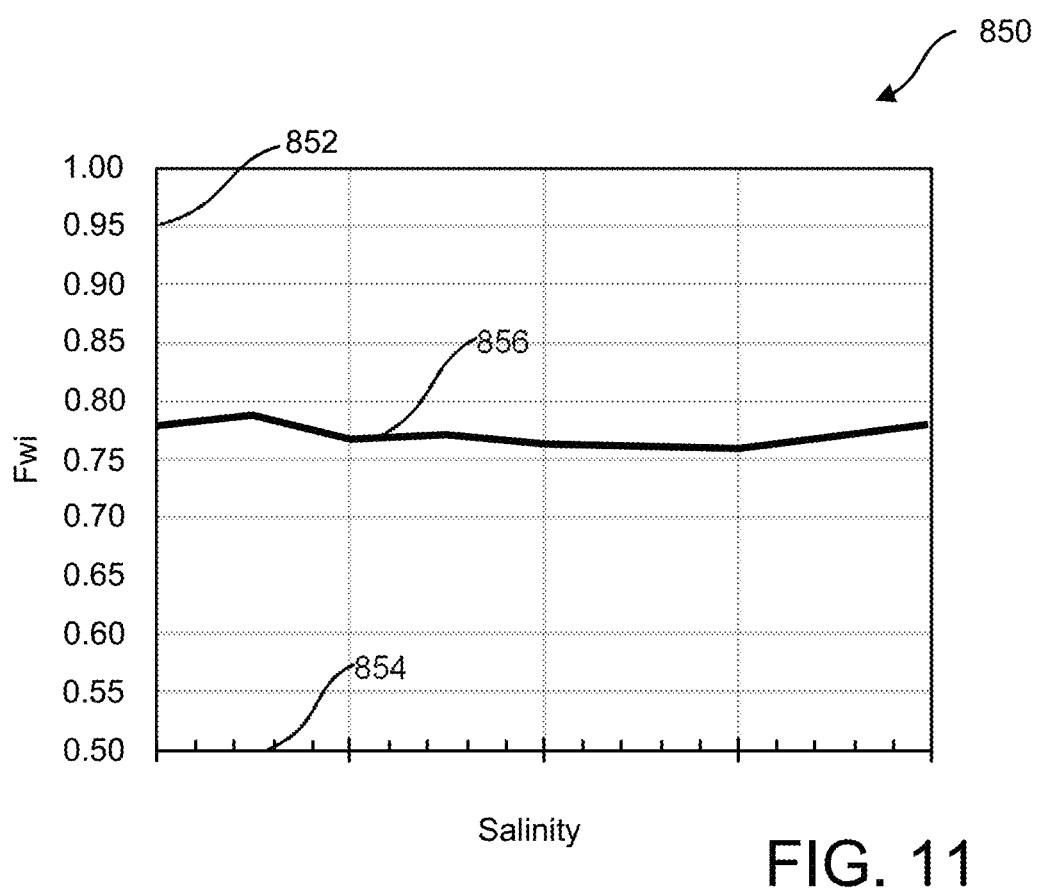

In contrast, FIG. 11 illustrates a plot 850 of results 856 in which salinity may have no correlative effect on the wettability of the system. Again, the vertical axis 852 represents wettability with respect to either one of water or oil. The horizontal axis 854 represents the salinity of the aqueous phase in a test system. As can be appreciated, this test system demonstrates no correlation between salinity and the wettability of the system. This may demonstrate that the system is not a candidate for enhanced petroleum recovery with a production water having modified or controlled salinity. As can be appreciated, determination of such system may allow for resources in relation to secondary oil recovery to be applied more efficiently to systems in which wettability is modified in relation to salinity of the aqueous phase.

While examples have been illustrated and described in detail in the drawings and foregoing description, such illustration and description is to be considered as exemplary and not restrictive in character. For example, certain examples described hereinabove may be combinable with other described examples and/or arranged in other ways (e.g., process elements may be performed in other sequences). Accordingly, it should be understood that only the preferred example and variants thereof have been shown and described and that all changes and modifications that come within the spirit of the disclosure are desired to be protected.

What is claimed is:

1. A method for performing a modified flotation test of a system corresponding to an oil reservoir of interest, comprising:
    adding to a test vessel:
    a solid phase sample comprising reservoir rock corresponding to the oil reservoir of interest;
    an aqueous phase sample corresponding to reservoir formation water found in the oil reservoir of interest;
    a gas phase sample that corresponds to a gas phase of the oil reservoir of interest; and
    an oil sample corresponding to an oil of the oil reservoir of interest;
    controlling a chemistry of contents of the test vessel to achieve an experimental pH value in the test vessel corresponding to conditions of the oil reservoir of interest;
    allowing contents of the test vessel after the adding steps to reside for at least a first residence time period while maintaining the experimental pH value in the test vessel corresponding to the oil reservoir of interest based on control of the chemistry of the contents of the test vessel;
    separating a first subset of solid phase sample particles in the aqueous phase sample from a second subset of solid phase sample particles in the oil sample from the test vessel after the first residence time period; and
    measuring relative amounts of the first subset of solid phase sample particles relative to the second subset of solid phase sample particles to determine a wettability of the system.

2. The method of claim 1, wherein the solid phase sample, the aqueous phase sample, the oil sample, and the gas phase sample are provided in the test vessel at a volumetric ratio approximating a relative ratio of the reservoir rock, reservoir formation water, the gas phase, and the oil in the reservoir of interest.

3. The method of claim 1, wherein the reservoir rock corresponding to the oil reservoir of interest comprises a sample obtained directly from the oil reservoir of interest.

4. The method of claim 1, wherein the aqueous phase sample comprises a produced water obtained directly from the oil reservoir of interest.

5. The method of claim 1, wherein the aqueous phase sample comprises a synthesized water.

6. The method of claim 1, wherein the oil sample comprises the oil obtained directly from the oil reservoir of interest.

7. The method of claim 1, wherein the gas phase comprises atmospheric gas comprising nitrogen, oxygen, argon, and carbon dioxide.

8. The method of claim 1, wherein controlling the chemistry of the contents of the test vessel comprises control of at least one of a composition, a temperature, or a pressure of the gas phase.

9. The method of claim 8, wherein controlling the chemistry of the gas phase comprises maintaining a vessel partial pressure of carbon dioxide in the test vessel at a level corresponding to a reservoir partial pressure of carbon dioxide in the reservoir of interest.

10. The method of claim 1, further comprising:
preparing a plurality of test vessels, each of the plurality of test vessels comprising a unique respective aqueous phase sample, wherein each corresponding one of the unique respective aqueous phase samples differ with respect to at least one of an amount of total dissolved solids (TD S);
measuring the relative amounts of the first subset of solid phase sample particles relative to the second subset of solid phase sample particles for each of the plurality of test vessels; and determining an equilibrium constant regarding the wettability of a system comprising the reservoir rock, the reservoir formation water, and the oil of the reservoir of interest based on the relative amounts of the first subset of solid phase sample particles relative to the second subset of solid phase sample particles for each of the plurality of test vessels.

11. The method of claim 10, wherein the equilibrium constant relates to a computational model regarding the reservoir of interest, and wherein the method further comprises:
using the equilibrium constant in the computational model for determining at least one property of an injected water for injection into the reservoir of interest to interact with a subterranean hydrocarbon reservoir of the reservoir of interest in a secondary production operation.

12. The method of claim 11, wherein the at least one property comprises an amount of total dissolved solids (TDS).

13. The method of claim 12, wherein the determining the at least one property of the injected water comprises determining an alteration to a produced water of the reservoir of interest to obtain the injected water.

14. The method of claim 10, wherein the equilibrium constant comprises an acid equilibrium constant derived by a plurality of basic test vessels having a pH greater than 7 and a base equilibrium constant derived by a plurality of acidic test vessels having a pH less than 5.

15. The method according to claim 1, further comprising:
preparing a plurality of test vessels, each of the plurality of test vessels comprising a unique respective aqueous phase sample, wherein each corresponding one of the unique respective aqueous phase samples differ with respect to at least one of an amount of total dissolved solids (TD S);
measuring the relative amounts of the first subset of solid phase sample particles relative to the second subset of solid phase sample particles for each of the plurality of test vessels; and
determining, based on the relative amounts of the first subset of solid phase sample particles relative to the second subset of solid phase sample particles for each of the plurality of test vessels, a given one of the unique respective aqueous phase samples that provides a nearest approximation of the first subset of solid phase sample particles and the second subset of solid phase sample particles being equal in relative amounts.

16. The method according to claim 15, further comprising:
determining at least one property of an injected water for injection into the reservoir of interest to interact with a subterranean hydrocarbon reservoir of the reservoir of interest in a secondary production operation based on the given one of the unique respective aqueous phase samples.

17. The method according to claim 1, further comprising:
expressing the wettability of the system as determined in the measuring step as a wettability value in relation to a wettability index.

18. A method for increasing oil recovery from a subterranean hydrocarbon reservoir formation, comprising:
injecting an injection water into the subterranean hydrocarbon reservoir formation at an injection well, wherein the injection water interacts with the subterranean hydrocarbon reservoir formation, and wherein the injection water comprises a recovery index value;
wherein the recovery index value corresponds to a wettability of the hydrocarbon reservoir formation in the presence of the injection water as determined by a modified flotation test that includes:
adding to a test vessel:
a solid phase sample comprising reservoir rock corresponding to the hydrocarbon reservoir formation;
an aqueous phase sample corresponding to reservoir formation water found in the hydrocarbon reservoir formation;
a gas phase sample that corresponds to a gas phase of the hydrocarbon reservoir formation;
an oil sample corresponding to an oil of the hydrocarbon reservoir formation;
controlling a chemistry of the test vessel to achieve an experimental pH value in the test vessel corresponding to conditions of the hydrocarbon reservoir formation;
allowing contents of the test vessel after the adding steps to reside for at least a first residence time period while maintaining the experimental pH value in the test vessel corresponding to the hydrocarbon reservoir formation based on control of the chemistry of the contents of the test vessel;
separating from the test vessel after the first residence time period a first subset of solid phase sample particles suspended in the aqueous phase sample from a second subset of solid phase sample particles suspended in the oil sample; and
measuring relative amounts of the first subset of solid phase sample particles relative to the second subset of solid phase sample particles to determine the wettability of the hydrocarbon reservoir formation.

19. The method of claim 18, further comprising:
recovering the injection water and a hydrocarbon from the subterranean hydrocarbon reservoir at a production well.

20. The method of claim 19, wherein the recovery index value comprises an indication that the injected water interacts with the subterranean hydrocarbon reservoir formation to result in the subterranean hydrocarbon reservoir formation being equally water wet and oil wet.

\* \* \* \* \*